United States Patent [19]

White

[11] 4,366,169
[45] Dec. 28, 1982

[54] USE OF PERFLUOROCARBONS AS WOUND TREATMENT

[75] Inventor: David C. White, Concordville, Pa.

[73] Assignee: Sun Tech, Inc., Philadelphia, Pa.

[21] Appl. No.: 228,642

[22] Filed: Jan. 26, 1981

Related U.S. Application Data

[63] Continuation-in-part of Ser. No. 52,041, Jun. 25, 1979, abandoned.

[51] Int. Cl.³ .................. A61K 31/02; A61K 31/025; A61K 31/34
[52] U.S. Cl. .................................... 424/285; 424/325; 424/350; 424/352; 424/DIG. 13
[58] Field of Search ............... 424/285, 325, 350, 352, 424/DIG. 13

[56] References Cited

U.S. PATENT DOCUMENTS

| | | | |
|---|---|---|---|
| 2,968,628 | 1/1961 | Reed | 252/305 |
| 3,911,138 | 10/1975 | Clark | 424/352 |
| 4,105,798 | 8/1978 | Moore et al. | 424/352 |
| 4,216,233 | 8/1980 | Stein | 424/350 |

OTHER PUBLICATIONS

Chemical Abstracts 62:11050(b), 1965.
Clark—"Blood Substitutes and Plasma Extenders", pp. 69–80 (1978).
Park—"Burn Wound Coverings—A Review, Biomat. Med. Dev., Art. Org., 6(1), 1–35 (1978).

*Primary Examiner*—Leonard Schenkman
*Attorney, Agent, or Firm*—J. Edward Hess; Donald R. Johnson; Patrick C. Baker

[57] ABSTRACT

Victims suffering certain types of wounds are treated by contacting the wound with a substantially fluorinated carbon material or a mono- or di-brominated derivative thereof containing molecular oxygen.

18 Claims, No Drawings

USE OF PERFLUOROCARBONS AS WOUND TREATMENT

CROSS-REFERENCE TO RELATED APPLICATIONS

This application is a continuation-in-part of application Ser. No. 52,041 filed June 25, 1979 by the present inventor, now abandoned.

BACKGROUND

A large number of persons suffer wounds of the type in which healing of the damaged tissue is limited by the amount of oxygen in the air normally exposed to the wound. Burns are the primary example and healing of damaged tissue characteristic of burns can be accelerated by increasing the amount of oxygen at the damaged tissue. Oxygen tents surrounding the entire victim or the burn area (hyperbaric chambers) have been used but not overly successfully because they present safety problems, the exchange rate of the oxygen and damaged tissue is not remarkably better, and they do not always eliminate bacterial infections which are prone to occur during the healing period.

The healing of many other types of wounds is subject to increased healing rate if the amount of oxygen exposed to the viable cells in and around the damaged tissue area is increased. These include such relatively minor wounds as ordinary cuts but also extend to surgical incisions, gunshot wounds, knife wounds, the skin opening left by the surgical removal of warts, bedsores (a form of ulcers), bone fractures where the broken bone penetrates the skin, the various cuts and injuries associated with automobile and other accidents, and the like. Most common such wounds are on the skin surface such as the arms, legs, roof of the mouth, etc., i.e., the body areas readily exposed to the atmosphere, but other areas such as the stomach, bones, lungs and the like can suffer similar type wounds, such as stomach ulcers, the actual break area in a broken bone, etc., where lack of oxygen slows down the healing rate.

The wounds described above all involve a discontinuity in the body tissue. It is this discontinuity, as in a cut finger, which needs to heal and the regeneration of the damaged or destroyed tissue is proportional to oxygen availability. The wounds described above do not encompass ordinary bruises where the problem is solely broken blood vessels resulting in black and blue marks but not in any tissue discontinuity.

Of the wounds described above burns are on the whole the most serious type. They often cover in the aggregate a larger area of the body but even individual burn areas are usually larger than the areas of the other wounds mentioned. Consequently they deserve special mention.

A large number of humans are burned each year, for example, one article "Burn Wound Coverings—A Review", by G. B. Park, appearing in Biomater. Med. Devices, Artif. Organs 6(1), 1–35, 1978 states that in the U.S. more than 2 million persons are burned seriously enough each year to need medical attention. It further states that some 70,000 persons each year require hospitalization, with 10,000 persons dying as a result of their injury.

The type of treatment for a burn is determined by the degree of the burn and the amount of surface area affected. With a serious burn one mode of treatment involves debridement, i.e., the removal of burned tissue by means involving e.g., surgery, mechanical or biochemical means. The latter is illustrated by enzymatic debridement using an enzymatic debriding agent which is usually applied in the form of an ointment. These agents are proteolytic enzymes that will selectively digest necrotic tissue without harming adjacent viable tissue. Other debridement techniques include the use of a tank filled with plain tap water maintained at a suitable temperature and strict sterile conditions. Once the human is in the tank, any dressings are removed and the burn cleaned and debrided. Afterwards the human is removed and covered with a sterile sheet and transferred to an adjacent dressing room of proper temperature and humidity.

Removal of the burned tissue can cause certain problems. Human skin, in addition to being an effective barrier against harmful external materials, prevents the body from losing its water. Such water loss, according to the article by Park, can cause intense catabolism which "manifests itself as increased heat production, increased water loss and nitrogen consumption, weight loss, negative nitrogen balance and loss of other cellular constituents derived largely from muscle." Intense catabolism can be fatal, and thus should be minimized or controlled.

Another problem, again according to the article by Park, is that "the preparation of a clean viable tissue area suitable for grafting is all-important and many lives may be lost by not securing a good take of a first graft in an extensively burned patient."

Articles which describe in greater detail the foregoing treatment and problems include the following: "Burn Injuries, Initial Evaluation and Treatment" Luterman, CUTIS 22(4):437–42, October 78; Care of the Burn Wound, Yarborough, M. F., CUTIS 22(4):447–52, October 78; Advances in Fluid Therapy and the Early Care of the Burn Patient, Pruitt, B. S. Jr., World J. Surg. 2(2):139–50, March 78; Emergency Burn Management, Gursel, E. et al. JACEP 7(5):209–12, May 78.

The use of water during debridement can be less than desirable. Water can be difficult to maintain in a pure state and microorganisms can easily grow in it. Yet chemicals, such as chlorine, used to prevent such growth could adversely affect unprotected tissue. Water containing microorganisms can facilitate the invasion of the body with harmful results. Thus, the burn victim, lacking his normal skin barrier, can be infected by the water contacting his unprotected tissue. Further, the water could adversely affect the preparation of a clean viable tissue area suitable for grafting by extracting helpful components from the contacted tissue.

While much of the foregoing discussion is expressed as a treatment of a human, no such limitation is intended. The wound treatments described and claimed hereinafter by the applicant are applicable to animal victims generally and not limited to humans.

SUMMARY OF THE INVENTION

The novel method of treating a wound involves contacting the wound with a molecular oxygen containing member of a family of materials popularly known as synthetic blood or blood substitutes, but not necessarily limited to these. Included in the foregoing classification are substantially fluorinated carbon materials, including perfluorocarbons, having an oxygen transport ability, emulsions of substantially fluorinated carbon materials having an oxygen transport ability, perfluorocarbons and combinations thereof. Mono- or di-brominated derivatives of the foregoing fluorinated carbon materials are also useful. The advantages of the synthetic blood materials are that they are non-toxic; can be highly saturated with oxygen; can be easily kept sterile and can be reused. It also can be easily maintained at a particular temperature, thereby providing for the victim's comfort. Because it can be highly saturated with oxygen, it promotes the healing of tissue. Further, because of its physical and chemical properties, a synthetic blood material may not extract a component from the tissue which is helpful for successful grafting. Also it could help avoid intense catabolism.

Another embodiment of the invention is the use of a dressing containing a synthetic blood material which dressing comes in contact with the wound. A dressing can be particularly useful for a small area wound. Other embodiments are disclosed hereinafter.

DETAILED DESCRIPTION

Useful preferred perfluorinated materials and methods for preparing them are described in the following U.S. Pat. Nos.: 4,105,798; 3,993,581; 3,962,439 and 3,911,138. The use of one particular member of the perfluorinated material class, i.e., perfluorodecalin, as a red cell substitute is described in particular detail in an article "Perfluorodecalin as a Red Cell Substitute", Clark, L. C., Blood Substitutes and Plasma Expanders, page 69–80. However, the substantially fluorinated and perfluorinated materials used in the treatment of a human suffering from a burn are not limited to those having a certain vapor pressure range, liver and/or spleen retention, etc., as required if used as a synthetic blood. The useful substantially fluorinated or perfluorinated materials are those which are generally liquids at temperatures and pressures, including ambient temperatures and pressures, suitable for contacting a victim.

Examples of some fluorinated materials suitable for use with this invention can include those which are broadly described as cyclic substantially fluorinated or perfluorohydrocarbons, including the substantially fluorinated or perfluoro derivatives of such $C_9$–$C_{18}$ polycyclic compounds as bicyclononanes (e.g., bicyclo[3.3.1]nonane, 2,6-dimethylbicyclo[3.3.1]nonane or 3-methylbicyclo[3.3.1]nonane), adamantane, methyl and dimethyladamantane, ethyladamantane, tetrahydrodicyclopentadiene, methyl and dimethylbicyclooctanes, ethylmethyladamantane, ethyldimethyladamantane, tetrahydrobinor-S, methyldiadamantane, triethyladamantane, triethyldiadamantane, pinane, camphane, 1,4,6,9-dimethanodecalin, bicyclo[4.3.2]undecane, bicyclo[5.3.0]decane and the like, or mixtures thereof). Other examples of suitable materials include perfluorotributylamine, perfluoro-2-butyltetrahydrofuran and other commercially available perfluoroethers. While some of the foregoing compounds are solid at ambient temperature they are soluble in ones which are liquid at ambient temperature and such a mixture could be used. Perfluorinated $C_8$ or lower materials and up to $C_{18}$ or higher materials can be used in this invention. Mixtures of various different perfluorinated materials can also be used. Although the specific percursors of the foregoing perfluorocarbons are unimportant for the present purpose they are usually the corresponding organic compounds in which most of the hydrogen atoms have been replaced with fluorine.

Perfluorinated means that substantially all of the corresponding hydrogen atoms of the carbon materials have been replaced by fluorine atoms. But while the foregoing perfluorinated materials (or perfluorocarbons) are preferred, other carbon materials which are substantially fluorinated can also be used in this invention. "Substantially fluorinated" indicates that most of the hydrogen atoms have been replaced by fluorine atoms, and that further replacement does not substantially increase the oxygen transport ability of the material. It is believed that this level is reached when about 80–90% of the hydrogen atoms have been replaced by fluorine atoms. In the aforementioned U.S. Pat. Nos. 3,911,138 and 4,105,798, the ability to transport oxygen is related to the solubility of oxygen in the materials and suggest that the perfluorinated materials will absorb 10–100 cc of oxygen per 100 cc of material at 25° C. and 760 milliliters of mercury. The substantially fluorinated carbon materials, i.e., perfluorocarbons, which can be used with this invention will have similar oxygen transport abilities.

Some of the fluorine atoms of the foregoing materials may be substituted by other halogen atoms such as bromine. Included among these compounds are, for example, monobrominated compounds such as 1-bromo-pentadecafluoro-4-isopropylcyclohexane and 1-bromo-pentadecafluoro-3-isopropylcyclopentane, or dibrominated derivatives thereof.

As indicated, perfluorinated means that substantially all the hydrogen atoms of the carbon material have been replaced by fluorine atoms (or bromine atoms in the case of the mono or dibrominated derivatives thereof described subsequently). It is preferred that at least 95% of the hydrogen atoms have been replaced, more preferably at least 98% and even more preferably essentially 100%.

Oxygen can be added to the material by many different means; one example of which would be to bubble 100% oxygen through the material.

Also, the perfluorocarbon material used in the treatment of a wound can be in the form of an emulsion containing the perfluorocarbon or brominated derivative thereof, water and a suitable emulsifier, and as an option other physiologically acceptable materials such as antibiotics. The high oxygen content of the perfluorocarbon can prevent or reduce microorganism growth in the water of the emulsion. Preparation of such an emulsion, selection of an emulsifier, and relative amounts of the components are discussed in greater detail in the aforementioned U.S. Pat. No. 4,105,798, which is incorporated herein by reference. The emulsion used in practicing this invention can also contain more than one kind of substantially fluorinated carbon material.

In practicing this invention any medicine which is used concurrently to treat a burn area should be inert, i.e., compatible with the perfluorocarbon or brominated derivatives thereof. Examples of medicines which have been used previously include silver nitrate and other antibiotics used to prevent or eliminate infection and the previously mentioned enzymatic debriding agent. Also, if the burn is caused by a chemical, the harmful chemical has to be completely removed from the victim prior to or concurrently with the use of the perfluorocarbon.

The contacting of a burn victim with the perfluorocarbon can occur by various means. For example, one embodiment involves the immersion of the victim in a bath of the material maintained at a suitable temperature for the victim's comfort. If necessary, the material, while in use or afterwards, is recirculated through cleansing means which remove tissue and other material coming from the victim. The immersion can also involve the use of a containment device such as a plastic bag which results in the immersion of only a portion of the victim, e.g., a hand, an arm or leg. The length of time of immersion depends in part, on the condition of the victim and the judgment of a medical practitioner. One advantage of using the aforementioned perfluorocarbon for contacting, and in particular via immersion, is that it also may assist in the control of body water lost through the exposed tissue, and thereby avoid intense catabolism. Another purpose of the contacting can be to flush the underlying wound bed prior to grafting. Apparently, any debris in the wound site discourages successful grafting.

The contacting of the victim with the perfluorocarbon (or brominated derivative thereof) can also occur by using a dressing containing the material. The purpose of the dressing is to contain the perfluorocarbon to the wound site. Although the plastic bag previously mentioned accomplishes this a dressing is usually applied immediately against the wound site or at least to the wound site and adjacent tissue area. The perfluorocarbon contained in the dressing, particularly if its vapor pressure is relatively low so that it does not evaporate readily, would help avoid a sticking problem. The liquid would lubricate the tissue and dressing and avoid any problem caused by drying. The dressing can be applied to the burn itself or can be e.g., a sheet which contacts most of the victim. "Dressing" as used herein is broadly defined to include any material suitable for coming in contact with a victim. While one may consider dressing equivalent to a sponge or to gauze in the sense of loosely woven cotton surgical dressing, no such limitation is intended. For example the dressing may also be a foam, spray or a gel containing the blood type material, freeze-dried pigskin or other suitable animal material. Normally the pigskin has to be reconstituted prior to use as a xenograft by soaking in sterile saline solution or some other suitable solution or the perfluorocarbon itself.

"Contacting" as used herein denotes a use in contrast to the internal use of certain perfluorinated materials as a blood substitute. Contacting as used herein refers to a local application and excludes the use of perfluorocarbons in the blood system. The contacting in most cases will be by application to the skin surface, as described before, but does not exclude application to non-skin surfaces by means other than the blood system. Examples of the latter applications include exposure of damaged bone tissue by surgery, applications to the stomach by tubes, applications to respiratory mucous surfaces by tubes, etc., and the like.

The invention claimed is:

1. A method of treating a victim having a wound the normal healing of which is accelerated by exposure to oxygen, which comprises contacting the wound with an effective amount of a liquid containing molecular oxygen and comprising a substantially fluorinated carbon material or a mono or dibrominated derivative thereof having an ability to transport oxygen, the contacting being by means other than the blood stream.

2. Method according to claim 1 wherein the wound is a burn.

3. Method according to claim 1 wherein the substantially fluorinated carbon material or derivative thereof is derived from a cyclic hydrocarbon.

4. Method according to claims 1, 2 or 3 wherein the treatment is applied to the surface of the skin.

5. Method according to claim 4 wherein the liquid also contains compatible medicine.

6. Method according to claim 3 wherein the treatment is preceded by a debridement.

7. An article useful for treating wounds the normal healing of which is accelerated by exposure to oxygen, comprising a dressing containing an effective amount of a liquid comprising a substantially fluorinated carbon material or a mono or dibrominated derivative thereof having an ability to transport oxygen.

8. Article according to claim 7 wherein the substantially fluorinated carbon material or derivative thereof is derived from a cyclic hydrocarbon.

9. Article according to claim 7 wherein the liquid also contains compatible medicine.

10. A method of treating a burn victim comprising contacting the burn with an effective amount of a liquid containing molecular oxygen and a material selected from the group consisting of a substantially fluorinated carbon material or a mono or di-brominated derivative thereof having an ability to transport oxygen, and an emulsion containing the material.

11. Method according to claim 10 wherein the substantially fluorinated carbon material is a perfluorinated carbon material.

12. Method according to claim 10 wherein the burn victim is a human.

13. An article, useful for treating burns, comprising a gauze or sponge dressing containing an effective amount of a liquid comprising a material selected from the group consisting of (a) a substantially fluorinated carbon material or a mono or di-brominated derivative thereof having an ability to transport oxygen, and (b) an emulsion containing the material.

14. Article according to claim 13 wherein the substantially fluorinated carbon material is a perfluorinated carbon material.

15. In the method of treating a burn victim wherein burned portions are subjected to debridement, the improvement which comprises contacting the burned portions of the victim with a liquid containing molecular oxygen and a material selected from the group consisting of a substantially fluorinated carbon material or a mono or di-brominated derivative thereof having an oxygen transport ability, and an emulsion containing the material.

16. The method of claim 15 wherein the substantially fluorinated carbon material is a perfluorinated carbon material.

17. A composition useful for treating burns, in the form of a foam, spray or gel, containing an effective amount of a liquid containing an oxygen transporting material selected from the group consisting of a substantially fluorinated carbon material or a mono or di-brominated derivative thereof, and an emulsion containing the material.

18. The article of claim 7 or 13 wherein the liquid contains molecular oxygen.

* * * * *